US006548458B2

(12) United States Patent
Loper

(10) Patent No.: US 6,548,458 B2
(45) Date of Patent: Apr. 15, 2003

(54) SUCCINIMIDE-ACID COMPOUNDS AND DERIVATIVES THEREOF

(75) Inventor: John T. Loper, Richmond, VA (US)

(73) Assignee: Ethyl Corporation, Richmond, VA (US)

(*) Notice: Subject to any disclaimer, the term of this patent is extended or adjusted under 35 U.S.C. 154(b) by 0 days.

(21) Appl. No.: 10/008,510

(22) Filed: Nov. 8, 2001

(65) Prior Publication Data

US 2002/0091068 A1 Jul. 11, 2002

Related U.S. Application Data

(62) Division of application No. 09/561,796, filed on May 1, 2000, now abandoned.

(51) Int. Cl.[7] .................. C10M 133/58; C10L 1/22; C07D 207/416
(52) U.S. Cl. .............. 508/291; 508/290; 508/231; 508/221; 44/348; 44/331; 548/546; 548/547
(58) Field of Search ................. 508/290, 291; 44/348; 548/546, 547

(56) References Cited

U.S. PATENT DOCUMENTS

| 3,903,005 A | | 9/1975 | Kablaoui et al. | |
|---|---|---|---|---|
| 4,218,328 A | | 8/1980 | Vaughhan | |
| 4,234,435 A | | 11/1980 | Meinhardt et al. | |
| 4,388,198 A | | 6/1983 | Butcosk | |
| 4,552,677 A | * | 11/1985 | Hopkins | 508/290 |
| 4,655,949 A | | 4/1987 | Landry | |
| 4,663,064 A | * | 5/1987 | Nalesnik et al. | 508/290 |
| 4,666,620 A | * | 5/1987 | Forsberg | 508/290 |
| 4,834,892 A | | 5/1989 | Damin et al. | |
| 4,919,685 A | | 4/1990 | Herbstman et al. | |
| 4,997,456 A | | 3/1991 | Malfer | |
| 5,266,081 A | | 11/1993 | Avery et al. | |
| 5,393,309 A | | 2/1995 | Cherpeck | |
| 5,536,434 A | * | 7/1996 | Venturello et al. | 510/375 |
| 5,620,486 A | | 4/1997 | Cherpeck | |
| 5,954,843 A | | 9/1999 | Cherpeck | |
| 5,993,497 A | * | 11/1999 | Cherpeck et al. | 44/347 |
| 6,114,542 A | * | 9/2000 | Cherpeck | 548/547 |

FOREIGN PATENT DOCUMENTS

| DE | 1 670 239 | 1/1971 |
|---|---|---|
| EP | 0 721 010 A1 | 7/1996 |
| FR | 2 044 305 A | 2/1971 |
| JP | 1994/06003782A A | 1/1994 |
| WO | WO94/21607 A1 | 9/1994 |
| WO | WO97/22582 A1 | 6/1997 |
| WO | WO00/02990 A1 | 1/2000 |

OTHER PUBLICATIONS

P. Weichert; The Effects of Succinyl–GABA–Derivatives on Experimental Seizures; & Monogr. Neural Sci. (1980), volume Date 1978, 5 (Epilepsy), STN Database Chemabs Online!; Database accession No. 96:115824 XP002174838 (Chemical Abstracts Service, Columbus, OH).
John P. Devlin; Antibiotic Actinonin. III. Synthesis of Structural Analogs of Actinonin by the Anhydride–Imide Method; Database Chemabs Online!; STN Database Accession No. 83:59249 XP002174839; (Chemical Abstracts Service, Columbus, OH).

* cited by examiner

Primary Examiner—Ellen M. McAvoy
(74) Attorney, Agent, or Firm—Dennis H. Rainear

(57) ABSTRACT

Succinimide-acid compounds prepared by reaction of hydrocarbyl-substituted succinic acylating agents with alpha-omega amino acids are disclosed, as well as derivatives thereof useful as lubricity additives, lubricant dispersants, friction modifiers, liquid hydrocarbonaceous fuel detergents, antioxidants and alkali and/or alkaline-earth metal detergents.

82 Claims, No Drawings

SUCCINIMIDE-ACID COMPOUNDS AND DERIVATIVES THEREOF

This application is a division of application Ser. No. 09/561,796, filed May 1, 2000, now abandoned.

TECHNICAL FIELD

The present invention is directed to novel succinimide-acid compounds prepared by reaction of hydrocarbyl-substituted succinic acylating agents with amino acids, as well as derivatives thereof useful as lubricity additives, lubricant dispersants, friction modifiers, liquid hydrocarbonaceous fuel detergents, antioxidants and alkali and/or alkaline-earth metal detergents.

BACKGROUND OF THE INVENTION

Hydrocarbyl-substituted succinic anhydride derivatives are widely used as fuel and lubricant additives. The hydrocarbyl-substituted succinic anhydride derivatives are typically prepared by reacting a hydrocarbyl-substituted succinic acylating agent with a polyamine to form a succinimide.

For example, hydrocarbyl-substituted succinic anhydrides and derivatives thereof prepared by the thermal reaction of a polyolefin and maleic anhydride, are described, for example in U.S. Pat. Nos. 3,361,673 and 3,676,089. Alternatively, hydrocarbyl-substituted succinic anhydrides can be prepared by the reaction of chlorinated polyolefins with maleic anhydride, are described, for example, in U.S. Pat. No. 3,172,892. Additional examples of hydrocarbyl-substituted succinic anhydrides and derivatives thereof can be found, for example, in U.S. Pat. Nos. 4,234,435; 4,997,456; 5,393,309 and 5,620,486.

U.S. Pat. Nos. 4,218,328; 4,655,949; and 4,834,892 disclose lubricating oil additives comprising metal salts of amino-acids.

None of these patents teach the succinimide-acids, or the derivatives thereof, of the present invention.

SUMMARY OF THE INVENTION

The succinimide-acid compounds of the present invention are prepared by reacting amino acids with a hydrocarbyl-substituted succinic acylating agent. The amino moiety of the amino acid undergoes reaction with the succinic acylating agent resulting in a succinimide moiety. This succinimide contains a pendant carboxylic acid moiety. The pendant carboxylic acid moiety can be utilized by reaction with various compounds including amines, alkoxylated amines and polyols to prepare products useful as dispersants, lubricity additives, friction modifiers, fuel detergents, antioxidants and alkali and/or alkaline-earth metal detergents.

DETAILED DESCRIPTION OF THE INVENTION

The Succinimide-Acid Compound

The succinimide-acid compounds of the present invention are prepared by reacting an amino acid with a hydrocarbyl succinic acylating agent in a reaction media. Suitable reaction media include, but are not limited to, organic solvents, such as toluene, or process oil. Water is a by-product of this reaction. The use of toluene allows for azeotropic removal of water.

The hydrocarbyl-substituted succinic acylating agents include the hydrocarbyl-substituted succinic acids, the hydrocarbyl-substituted succinic anhydrides, the hydrocarbyl-substituted succinic acid halides (especially the acid fluorides and acid chlorides), and the esters of the hydrocarbyl-substituted succinic acids and lower alcohols (e.g., those containing up to 7 carbon atoms), that is, hydrocarbyl-substituted compounds which can function as carboxylic acylating agents. Of these compounds, the hydrocarbyl-substituted succinic acids and the hydrocarbyl-substituted succinic anhydrides and mixtures of such acids and anhydrides are generally preferred, the hydrocarbyl-substituted succinic anhydrides being particularly preferred.

The acylating agent for producing the hydrocarbyl substituted acylating agent is preferably made by reacting a polyolefin of appropriate molecular weight (with or without chlorine) with maleic anhydride. However, similar carboxylic reactants can be employed such as maleic acid, fumaric acid, malic acid, tartaric acid, itaconic acid, itaconic anhydride, citraconic acid, citraconic anhydride, mesaconic acid, ethylmaleic anhydride, dimethylmaleic anhydride, ethylmaleic acid, dimethylmaleic acid, hexylmaleic acid, and the like, including the corresponding acid halides and lower aliphatic esters.

The hydrocarbyl-substituted succinic anhydrides are typically prepared by heating a mixture of maleic anhydride and an aliphatic olefin at a temperature of about 175–275° C. The molecular weight of the olefin can vary widely depending upon the intended use of the substituted succinic anhydrides. Typically, the substituted succinic anhydrides will have a hydrocarbyl group of from 8–500 carbon atoms. Friction modifiers, lubricity additives, antioxidants and fuel detergents generally have a hydrocarbyl group of about 8–100 carbon atoms, while substituted succinic anhydrides used to make lubricating oil dispersants will typically have a hydrocarbyl group of about 40–500 carbon atoms. With the very high molecular weight substituted succinic anhydrides, it is more accurate to refer to number average molecular weight (Mn) since the olefins used to make these substituted succinic anhydrides are a mixture of different molecular weight components resulting from the polymerization of low molecular weight olefin monomers such as ethylene, propylene and isobutylene.

The low molecular weight alkyl-substituents typically contain from 8 to 100 carbon atoms, preferably from 12 to 30 carbon atoms, more preferably 16 to 26 carbon atoms. The low molecular weight alkyl substituents include alpha-olefins having single carbon number fraction between C9 and C30 or a mixture of carbon number fractions between C9 and C30. The alpha-olefins may be isomerized to produce an olefin containing an internal double bond, which may be used for alkylation of the hydroxyaromatic compound. Also useful as the low molecular weight alkyl substituents are oligomers of 1-olefins.

Examples of such compounds include tridecylsuccinic acid, pentadecylsuccinic acid, tetradecenylsuccinic acid, hexadecenylsuccinic acid, dodecylsuccinic acid, tetradecylsuccinic acid, hexadecylsuccinic acid, octadecenylsuccinic acid, tetrapropylene-substituted succinic acid, docosenylsuccinic acid and mixtures thereof. Preferred acylating agents are alkyl and/or alkenyl succinic anhydrides in which the alkyl or alkenyl group is substantially straight chain in configuration and contains 12 to 30 carbon atoms, and more preferably an average of about 16 to about 26 carbon atoms. An especially preferred acylating agent of this type is octadecenylsuccinic acid or anhydride.

Still another preferred hydrocarbyl-substituted acylating agent is an alkyl- or alkenylsuccinic acid or anhydride in which the alkyl or alkenyl group is bifurcated on the beta-carbon atom and is composed of two substantially linear chains. Preferred alkyl groups of this type may be represented by the formula

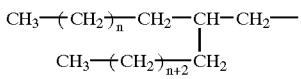

where n is an integer in the range of 2 to 10. A preferred group of such bifurcated alkenyl groups may be represented by the formula

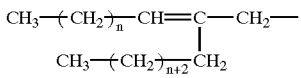

where n is an integer in the range of 2 to 10. It will be understood and appreciated that the double bond in such alkenyl group may be isomerized to different positions from that depicted (which is the preferred position) by treating the alkenylsuccinic acid or anhydride with an isomerization catalyst such as silica gel, a trialkylborane, or the like. Such alkyl- and alkenyl substituted succinic acids and anhydrides can be formed from dimerized 1-olefins such as by dimerizing 1-hexene, 1-heptene, 1-octene, 1-nonene, 1-decene, 1-undecene, 1-dodecene, 1-tetradecene, 4-methyl-1-pentene, 6-methyl-1-heptene, 5-ethyl-1-decene, or 3,5,5-trimethyl-1-undecene with an aluminum alkyl dimerization catalyst according to known procedures. See for example Ziegler et al, Ann. 629, 121–166 (1960) all disclosure of which is incorporated herein by reference. The resultant dimerized olefin (sometimes referred to as a vinylidene olefin) is then used to alkylate maleic anhydride or an ester of maleic acid, etc., to form the alkenyl-substituted succinic acid compound by the "ene" reaction. See in this connection Hoffman, Angew. Chem., Int. Ed. (English), 8, 556–577 (1969); Snider, J. Org. Chem., 39, 255 (1974); and Keung et al, J. Chem. Educ., 49. 97–100 (1972), all disclosures of which are incorporated herein by reference. As is well known, the "ene" reaction may be facilitated by the use of a catalyst such as aluminum trichloride, alkyl aluminum sesquichloride or the like. To form the bifurcated alkyl substituent, the bifurcated alkenyl group of the resultant alkenyl-substituted succinic acid compound may be hydrogenated to saturate the double bond.

Similarly suitable alkyl- or alkenylsuccinic acids or anhydrides in which the alkyl or alkenyl group is bifurcated on the beta-carbon atom into two branches can be formed in analogous fashion using co-dimerized 1-olefin such as by co-dimerizing 1-butene and 1-octene, 1-hexene and 1-decene, 1-pentene and 1-dodecene, 4-methyl-1-pentene and 1-tetradecene, 1-octene and 1-decene, 1-nonene and 1-decene, 1-decene and 1-dodecene, 1-dodecene and 1-tetradecene, 2,7-dimethyl-1-octene and 1-decene, 2,7-dimethyl-1-octene and 1-dodecene, 1-tetradecene and 1-pentadecene, etc., using a co-dimerization catalyst such as an aluminum alkyl. Such co-dimerized olefins are then used in the "ene" reaction in the same manner as described above. Hydrogenation of the alkenyl succinic acid compound (anhydride, ester, etc.) yields the corresponding bifurcated alkyl succinic acid compound.

The mole ratio of maleic anhydride to olefin can vary widely. It may vary, for example, from 5:1 to 1:5, a more preferred range is 3:1 to 1:3. With the high molecular weight olefins such as polyisobutylene having a number average molecular weight of 500 to 7000, preferably 800 to 3000 or higher and the ethylene-alpha-olefin copolymers, the maleic anhydride is preferably used in stoichiometric excess, e.g. 1.1–5 moles maleic anhydride per mole of olefin. The unreacted maleic anhydride can be vaporized from the resultant reaction mixture.

With the lower molecular weight olefins, e.g. Mn of 100–350, either reactant can be used in excess or they can be reacted in a 1:1 mole ratio. Typically an excess of olefin is used, e.g. 1.1–3 moles of olefin per mole maleic anhydride.

The hydrocarbyl-substituted succinic anhydrides of the present invention include polyalkyl or polyalkenyl succinic anhydrides prepared by the reaction of maleic anhydride with the desired polyolefin or chlorinated polyolefin, under reaction conditions well known in the art. For example, such succinic anhydrides may be prepared by the thermal reaction of a polyolefin and maleic anhydride, as described, for example in U.S. Pat. Nos. 3,361,673 and 3,676,089 and European Patent 0623631 B 1. Alternatively, the substituted succinic anhydrides can be prepared by the reaction of chlorinated polyolefins with maleic anhydride, as described, for example, in U.S. Pat. No. 3,172,892. A further discussion of hydrocarbyl-substituted succinic anhydrides can be found, for example, in U.S. Pat. Nos. 4,234,435; 5,620,486 and 5,393,309. Typically, these hydrocarbyl-substituents will contain from 40 to 500 carbon atoms.

Polyalkenyl succinic anhydrides may be converted to polyalkyl succinic anhydrides by using conventional reducing conditions such as catalytic hydrogenation. For catalytic hydrogenation, a preferred catalyst is palladium on carbon. Likewise, polyalkenyl succinimides may be converted to polyalkyl succinimides using similar reducing conditions.

The polyalkyl or polyalkenyl substituent on the succinic anhydrides employed in the invention is generally derived from polyolefins which are polymers or copolymers of mono-olefins, particularly 1-mono-olefins, such as ethylene, propylene and butylene. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, polyisobutene, and the polyalphaolefins produced from 1-octene and 1-decene.

A particularly preferred hydrocarbyl substituent is one derived from polyisobutene. Suitable polyisobutenes for use in preparing the succinimide-acids of the present invention include those polyisobutenes that comprise at least about 20% of the more reactive methylvinylidene isomer, preferably at least 50% and more preferably at least 70%. Suitable polyisobutenes include those prepared using $BF_3$ catalysts. The preparation of such polyisobutenes in which the methylvinylidene isomer comprises a high percentage of the total composition is described in U.S. Pat. Nos. 4,152,499 and 4,605,808.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents such as pyridyl, furyl, thienyl and imidazolyl. In general, no more than two, preferably no more than one, non-hydrocarbon substituent will be present for every ten carbon atoms in the hydrocarbyl group; typically, there will be no nonhydrocarbon substituents in the hydrocarbyl group.

For purposes of the present invention, the term hydrocarbyl-substituted succinic anhydrides includes olefin copolymers grafted with maleic anhydride. Suitable anhydride grafted olefin copolymers are well known in the art, for example, U.S. Pat. No. 4,863,623. Preferred as the olefin copolymer substrate are copolymers of ethylene and one or more $C_3$ to $C_{23}$ alpha-olefins. Copolymers of ethylene and propylene are most preferred. Other alpha-olefins suitable for use in place of propylene to form the copolymer or to be used in combination with ethylene and propylene to form a terpolymer include 1-butene, 1-pentene, 1-hexene, 1-octene and styrene; $\alpha,\omega$-diolefins such as 1,5-hexadiene, 1,6-heptadiene, 1,7-octadiene; branched chain alpha-olefins such as 4-methylbutene-1, 5-methylpentene-1 and 6-methylheptene-1; and mixtures thereof.

More complex polymer substrates, often designated as interpolymers, may be prepared using a third component. The third component generally used to prepare an interpolymer substrate is a polyene monomer selected from non-conjugated dienes and trienes. The non-conjugated diene component is one having from 5 to 14 carbon atoms in the chain. Preferably, the diene monomer is characterized by the presence of a vinyl group in its structure and can include cyclic and bicyclo compounds. Representative dienes include 1,4-hexadiene, 1,4-cyclohexadiene, dicyclopentadiene, 5-ethylidene-2-norbornene, 5-methylene-2-norborene, 1,5-heptadiene, and 1,6-octadiene. A mixture of more than one diene can be used in the preparation of the interpolymer. A preferred non-conjugated diene for preparing a terpolymer or interpolymer substrate is 1,4-hexadiene.

The triene component will have at least two non-conjugated double bonds, and up to about 30 carbon atoms in the chain. Typical trienes useful in preparing the interpolymer of the invention are 1-isopropylidene-3$\alpha$,4,7,7$\alpha$-tetrahydroindene, 1-isopropylidenedicyclopentadiene, dihydro-isodicyclopentadiene, and 2-(2-methylene-4-methyl-3-pentenyl)[2.2.1]bicyclo-5-heptene.

Ethylene-propylene or higher alpha-olefin copolymers typically comprise from about 15 to 80 mole percent ethylene and from about 85 to 20 mole percent $C_3$ to $C_{23}$ alpha-olefin with the preferred mole ratios being from about 35 to 75 mole percent ethylene and from about 65 to 25 mole percent of a $C_3$ to $C_{23}$ alpha-olefin, with the more preferred proportions being from 50 to 70 mole percent ethylene and 50 to 30 mole percent $C_3$ to $C_{23}$ alpha-olefin, and the most preferred proportions being from 55 to 65 mole percent ethylene and 45 to 35 mole percent $C_3$ to $C_{23}$ alpha-olefin.

Terpolymer variations of the foregoing polymers may contain from about 0.1 to 10 mole percent of a non-conjugated diene or triene.

The polymer substrate, that is the ethylene copolymer or terpolymer, is an oil-soluble, linear or branched polymer having a number average molecular weight from about 1000 to 20,000 as determined by gel permeation chromatography and universal calibration standardization, with a preferred number average molecular weight range of 6,000 to 10,000.

The terms polymer and copolymer are used generically to encompass ethylene copolymers, terpolymers or interpolymers. These materials may contain minor amounts of other olefinic monomers so long as the basic characteristics of the ethylene copolymers are not materially changed.

The polymerization reaction used to form the ethylene-olefin copolymer substrate is generally carried out in the presence of a conventional Ziegler-Natta or metallocene catalyst system. The polymerization medium can include solution, slurry, or gas phase processes, as known to those skilled in the art. When solution polymerization is employed, the solvent may be any suitable inert hydrocarbon solvent that is liquid under reaction conditions for polymerization of alpha-olefins; examples of satisfactory hydrocarbon solvents include straight chain paraffins having from 5 to 8 carbon atoms, with hexane being preferred. Aromatic hydrocarbons, preferably aromatic hydrocarbons having a single benzene nucleus, such as benzene and toluene; and saturated cyclic hydrocarbons having boiling point ranges approximating those of the straight chain paraffinic hydrocarbons and aromatic hydrocarbons described above, are particularly suitable. The solvent selected may be a mixture of one or more of the foregoing hydrocarbons. When slurry polymerization is employed, the liquid phase for polymerization is preferably liquid propylene. It is desirable that the polymerization medium be free of substances that will interfere with the catalyst components.

The grafting reaction to form the maleic anhydride grafted olefin copolymers is generally carried out with the aid of a free-radical initiator either in solution or in bulk, as in an extruder or intensive mixing device. When the polymerization is carried out in hexane solution, it is economically convenient to carry out the grafting reaction as described in U.S. Pat. Nos. 4,340,689, 4,670,515 and 4,948,842. The resulting polymer is characterized by having succinic anhydride functionality randomly within its structure.

In the bulk process for forming the grafted olefin copolymers, the olefin copolymer is fed to rubber or plastic processing equipment such as an extruder, intensive mixer or masticator, heated to a temperature of 150° to 400° C. and the maleic anhydride and free-radical initiator are separately co-fed to the molten polymer to effect grafting. The reaction is carried out optionally with mixing conditions to effect shearing and grafting of the ethylene copolymers according to U.S. Pat. No. 5,075,383. The processing equipment is generally purged with nitrogen to prevent oxidation of the polymer and to aid in venting unreacted reagents and byproducts of the grafting reaction. The residence time in the processing equipment is sufficient to provide for the desired degree of functionalization and to allow for purification of the functionalized copolymer via venting. Mineral or synthetic lubricating oil may optionally be added to the processing equipment after the venting stage to dissolve the functionalized copolymer.

The free-radical initiators which may be used to graft the maleic anhydride to the polymer backbone include peroxides, hydroperoxides, peresters, and azo compounds, preferably those which have a boiling point greater than 100° C. and decompose thermally within the grafting temperature range to provide free radicals. Representatives of these free-radical initiators are azobutyronitrile, dicumyl peroxide, 2,5-dimethylhexane-2,5-bis-tertiarybutyl peroxide and 2,5-dimethyl-hex-3-yne-2,5-bis-tertiary-butyl peroxide. The initiator is typically used in an amount of between about 0.005% and about 1% by weight based on the weight of the reaction mixture.

Other methods known in the art for effecting reaction of ethylene-olefin copolymers with maleic anhydride, such as halogenation reactions, thermal or "ene" reactions or mixtures thereof, can be used instead of the free-radical grafting process. Such reactions are conveniently carried out in mineral oil or bulk by methods known in the art. For example, heating the reactants at temperatures of 250 to 400° C. under an inert atmosphere to avoid the generation of free radicals and oxidation byproducts. "Ene" reactions are a preferred method of grafting when the ethylene-olefin copolymer contains unsaturation. Depending upon the amount of anhydride functionality desired, it may be necessary to follow or proceed the "ene" or thermal graft reaction with a free radical graft reaction.

The amino acids used in the present invention can be represented by the following formula:

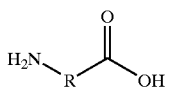

wherein R is an alkyl group, having from 1 to 12 carbon atoms, or an aryl group.

Suitable amino acids include alpha-omega amino acids such as glycine, beta-alanine, gamma-aminobutyric acid, 6-aminocaproic acid, 7-aminoheptanoic acid, aminocaprylic acid, 11-aminoundecanoic acid and 12-aminododecanic acid Suitable aromatic amino acids include those compounds wherein R comprises benzene, naphthalene and benzophenone. Representative examples of aromatic amino acids useful in the present invention include 2-aminobenzoic acid, 3-aminobenzoic acid, 4-aminobenzoic acid, 4-(aminomethyl) benzoic acid, 2-amino-3-methylbenzoic acid, 2-amino-5-methylbenzoic acid, 2-amino-6-methylbenzoic acid, 3-amino-2-methylbenzoic acid, 3-amino-4-methylbenzoic acid, 4-amino-2-methylbenzoic acid, 6-aminonicotinic acid, 3-amino-2-naphthoic acid, 2-aminobenzophenone-2'-carboxylic acid and 2-(2aminobenzoyl)benzoic acid.

The molar ratio of anhydride to amino acid ranges from 1:10 to 1:1, preferably the molar ratio of anhydride to amino acid is 1:1.

The succinimide-acid compounds useful in the present invention are prepared by combining the hydrocarbyl-substituted succinic acylating agent and at least one amino acid with a reaction media in a suitable reaction vessel and reacting at a temperature and for a time sufficient to form a succinimide. These reaction conditions are readily determinable by a person skilled in the art. When the reaction media used is process oil, the reaction mixture is typically heated to between 120 and 180° C. under nitrogen. The reaction generally requires 2 to 5 hours for complete removal of water and formation of the succinimide product. When toluene (or other organic solvent) is used as the reaction media, the reflux temperature of the water/toluene (solvent) azeotrope determines the reaction temperature.

Representative examples of suitable preparation methods for the succinimide-acids are as follows:

Example: Preparation of SAcid-2

A 2 L round bottom flask equipped with overhead stirrer, condenser, and Dean-Stark trap was charged with 590 g of an alkenyl succinic anhydride (Acid #0.35 meq KOH/g), 26.7 g of 6-amino caproic acid and 300 g of toluene. The reaction mixture was heated at reflux. After 4 hours 3.2 mL of water was collected. FTIR indicated that succinimide was formed. The reaction mixture was filtered and concentrated in vacuo to afford 632 g of product.

Example: Preparation of SAcid-3

A 3 L resin kettle equipped with overhead stirrer, Dean Stark trap, condenser, and thermometer under a nitrogen atmosphere was charged with 956 g of an alkenyl succinic anhydride (Acid #0.35 meq KOH/g), 43.3 g of 6-amino caproic acid and 514 g of process oil. The mixture was heated with stirring under nitrogen to 140° C. over 1 hour. The reaction temperature was then raised over 1 hour to 160° C. and held at this temperature for 3 hours. FTIR indicated that succinimide was formed. The reaction mixture was cooled and filtered to afford 1483 g of product.

The molar ratio of anhydride to amino acid used in preparing the succinimide-acid compounds of Table I was approximately 1:1.

TABLE I

Synthesized Succinimide-acid (SAcid) compounds:

| Sample | Anhydride | Acid | Reaction Media |
| --- | --- | --- | --- |
| SAcid-1 | $C_{16-18}ASA^1$ | 6-amino caproic acid | Toluene |
| SAcid-2 | 2100 PIBSA[2] | 6-amino caproic acid | Toluene |
| SAcid-3 | 2100 PIBSA | 6-amino caproic acid | Process Oil |
| SAcid-4 | 900 PIBSA[3] | 6-amino caproic acid | Toluene |
| SAcid-5 | 2100 PIBSA | 4-amino butyric acid | Process Oil |
| SAcid-6 | 2100 PIBSA | 11-amino undecanoic acid | Process Oil |
| SAcid-7 | 2100 PIBSA | gamma-amino butyric acid | Process Oil |
| SAcid-8 | $C_{16-18}ASA$ | 11-amino undecanoic acid | Process Oil |
| SAcid-9 | 2100 PIBSA | 4-aminobenzoic acid | Process Oil |
| SAcid-10 | 1300 PIBSA[4] | 6-aminocaproic acid | Process Oil |

[1]C16–18 alkenyl succinic anhydride
[2]polyisobutenyl succinic anhydride derived from polyisobutene having a number average molecular weight of approximately 2100.
[3]polyisobutenyl succinic anhydride derived from polyisobutene having a number average molecular weight of approximately 900.
[4]polyisobutenyl succinic anhydride derived from polyisobutene having a number average molecular weight of approximately 1300.

The succinimide-acids of the present invention may be reacted with additional compounds or polymers to produce products suitable for numerous applications. Suitable reactants include those capable of reacting with the acid group of the succinimide-acid, such as compounds, oligomers and polymers containing amine and/or hydroxy functionality to form succinimide-amides, succinimide-esters and mixtures thereof.

Preparation of Succinimide-Acid Derivatives

To prepare succinimide-acid derivatives, the succinimide-acid compound can reacted with a compound containing at least one primary or secondary amine capable of reacting with said succinimide-acid to form the succinimide-amide or a hydroxy containing compound to form an ester. Mixtures of succinimide-amides and succinimide-esters may be formed by reaction of the succinimide-acid compound with a hydroxyamine compound containing at least one primary or secondary amine capable of reacting with said succinimide-acid and containing at least one hydroxy group capable of reacting with said succinimide-acid.

Reaction of the pendant carboxylic acid moiety of the succinimide-acid compound with the amine results in the formation of an amide bond. The reaction is conducted at a temperature and for a time sufficient to form the succinimide-amide reaction product. These reaction conditions can readily be determined by one skilled in the art.

Typically, the reaction is conducted in a suitable reaction media such as an organic solvent, for example, toluene, or process oil. The reaction is typically conducted at a temperature of from 110 to 180° C. for 2 to 10 hours.

The reactants are preferably used in amounts so as to provide a ratio of acid groups on the succinimide-acid compound to polyamine in the range of from n:1 to 1:1 where n is the number of reactive nitrogen atoms (i.e., unhindered primary and secondary amines capable of reacting with the acid groups of the succinimide-acid) within the polyamine.

The preferred amines are polyamines and hydroxyamines. Examples of polyamines that may be used include, but are not limited to, aminoguanidine bicarbonate (AGBC), diethylene triamine (DETA), triethylene tetramine (TETA), tetraethylene pentamine (TEPA), pentaethylene hexamine (PEHA) and heavy polyamines. A heavy polyamine is a mixture of polyalkylenepolyamines comprising small amounts of lower polyamine oligomers such as TEPA and PEHA but primarily oligomers with 7 or more nitrogens, 2 or more primary amines per molecule, and more extensive branching than conventional polyamine mixtures.

Polyamines that are also suitable in preparing the dispersants of the present invention include N-arylphenylenediamines, such as N-phenylphenylenediamines, for example, N-phenyl-1,4-phenylenediamine, N-phenyl-1,3-phenylendiamine, and N-phenyl-1,2-phenylenediamine; aminothiazoles such as aminothiazole, aminobenzothiazole, aminobenzothiadiazole and aminoalkylthiazole; aminocarbazoles; aminoindoles; aminopyrroles; amino-indazolinones; aminomercaptotriazoles; aminoperimidines; aminoalkyl imidazoles, such as 1-(2-aminoethyl) imidazole, 1-(3-aminopropyl) imidazole; and aminoalkyl morpholines, such as 4-(3-aminopropyl) morpholine. These polyamines are described in more detail in U.S. Pat. Nos. 4,863,623; and 5,075,383. These polyamines can provide additional benefits, such as antiwear and antioxidancy, to the final products.

Additional polyamines useful in forming the succinimide-amides of the present invention include polyamines having at least one primary or secondary amino group and at least one tertiary amino group in the molecule as taught in U.S. Pat. Nos. 5,634,951 and 5,725,612. Examples of suitable polyamines include N,N,N",N"-tetraalkyldialkylenetriamines (two terminal tertiary amino groups and one central secondary amino group), N,N,N',N"-tetraalkyltrialkylenetetramines (one terminal tertiary amino group, two internal tertiary amino groups and one terminal primary amino group), N,N,N',N",N'"-pentaalkyltrialkylenetetramines (one terminal tertiary amino group, two internal tertiary amino groups and one terminal secondary amino group), tris(dialkylaminoalkyl) aminoalkylmethanes (three terminal tertiary amino groups and one terminal primary amino group), and like compounds, wherein the alkyl groups are the same or different and typically contain no more than about 12 carbon atoms each, and which preferably contain from 1 to 4 carbon atoms each. Most preferably these alkyl groups are methyl and/or ethyl groups. Preferred polyamine reactants of this type include dimethylaminopropylamine (DMAPA) and N-methyl piperazine.

Hydroxyamines suitable for use in the present invention include compound, oligomer or polymer containing at least one primary or secondary amine capable of reacting with the succinimide-acid to form a succinimide-amide and also containing at least one hydroxy group capable of reacting with the succinimide-acid to form a succinimide-ester. Examples of hydroxyamines suitable for use in the present invention include aminoethylethanolamine (AEEA), aminopropyldiethanolamine (APDEA), ethanolamine, diethanolamine (DEA), partially propoxylated hexamethylene diamine (for example HMDA-2PO or HMDA-3PO), 3-amino-1,2-propanediol, tris(hydroxymethyl)aminomethane, and 2-amino-1,3-propanediol. When hydroxyamines are used, the reaction products of the succinimide-acid and the hydroxyamine may contain mixtures of succinimide-amides and succinimide-esters.

Reaction of the pendant carboxylic acid moiety of the succinimide-acid compound with the polyhydroxy compound results in the formation of an ester bond. The reaction is conducted at a temperature and for a time sufficient to form the succinimide-ester reaction product. Typically, the reaction is conducted in a suitable reaction media such as an organic solvent, for example, toluene, or process oil. The reaction is typically conducted at a temperature of from 110 to 180° C. for 2 to 10 hours.

The reactants are preferably used in amounts so as to provide a ratio of acid groups on the succinimide-acid compound to polyhydroxy compound in the range of from n:1 to 1:1 where n is the number of hydroxyl groups in the polyhydroxy compound. It is preferred that the molar ratio of succinimide-acid compound to polyhydroxy compound be between 3:1 and 1:1, more preferably the molar ratio of succinimide-acid compound to polyhydroxy compound is 2:1.

Examples of alkoxylated amines that may be used include fully alkoxylated amines, i.e., no primary or secondary amine groups remain, such as propoxylated hexamethylene diamine (HMDA-4PO), propoxylated triethylene tetramine (TETA-PO), tetrakis(2-hydroxypropyl)ethylenediamine (EDA-4PO) and triethanolamine (TEA).

Suitable polyols include glycerol, sorbitol, pentaerythitol, mannitol and polyalkylene glycols.

Some contemplated uses of the succinimide-acids, and derivatives thereof, of the present invention include lubricity additives, lubricant dispersants, friction modifiers, liquid hydrocarbonaceous fuel detergents, antioxidants and alkali and/or alkaline-earth metal detergents. Typically, the usefulness of the reaction products in the above-identified applications will be determined by the selection of the hydrocarbyl-substituted succinic acylating agent, the amino acids, and the amines or polyhydroxy compounds when used.

Preparation of Dispersant Additives

The succinimide-acid compounds of the present invention may be utilized to prepare compounds suitable for use as dispersants in lubricating oil formulations or to increase the molecular weight of existing amine-based dispersant compounds. The pendant carboxylic acid moiety of the succinimide-acid compound can undergo reaction with polyamines, partially alkoxylated polyamines and/or alkoxylated amines to generate reaction products useful as dispersants. Reaction of polyamines or partially alkoxylated polyamines with the succinimide-acid compound results in a succinimide-amide compound. Reaction of fully alkoxylated amines with the succinimide-acid compound results in a succinimide-ester compound. Reaction of an amine dispersant with the succinimide-acid compound results in a succinimide-amide compound.

When preparing the succinimide-amide and succinimide-ester reaction products for use as lubricating oil dispersants, it is preferred that the succinimide-acid compound used is formed from a hydrocarbyl-substituted succinic acylating agent wherein the hydrocarbyl group on the substituted succinic acylating agent has a number average molecular weight of from 100 to 20,000. Preferred hydrocarbyl-substituted succinic acylating agents for use in preparing the succinimide-amide reaction products useful as lubricating oil dispersants include polyalkenyl succinic anhydrides having a number average molecular weight of from 100 to 7000, preferably 500 to 3000, and maleic anhydride grafted ethylene-alpha-olefin copolymers having a number average molecular weight of from 1000 to 20,000, preferably 6000 to 10,000.

Dispersants in the lubricating oil suspend thermal decomposition and oxidation products, such as soot and sludge, and reduce or retard the formation of deposits on lubricated surfaces.

Examples of Succinimide-Amide Dispersants

The succinimide-amide reaction products set forth in Table II were prepared as follows:

Amines and the succinimide-acid compounds, as set forth in Table II, were combined with process oil in a suitable reaction vessel and heated to between 160 and 180° C. under nitrogen. The reaction generally required 4 to 8 hours for formation of the amide product. Formation of the succinimide-amide can be confirmed by FTIR or the total acid number (TAN) of the final product can be determined to estimate the amount of unreacted acid. The molar ratio of succinimide-acid compound to amine compound used in preparing the succinimide-amides is set forth in the Table.

A representative example of a suitable preparation method for the succinimide-amides is as follows:

Example: Preparation of SAmide-3

A 1000 mL resin kettle equipped with overhead stirrer, Dean Stark trap, and thermometer was charged with 271 g of Sacid-2, 5.7 g of tetraethylenepentamine and 74.3 g of process oil. The mixture was heated to 160° C. with stirring and under a continual nitrogen purge. The reaction mixture was held at this temperature for 4 hours. Residual water was removed in vacuo to afford 303.6 g of product.

TABLE II

Succinimide-Amide (SAmide) Reaction Products

| Sample | Succinimide-Acid | Amine | Ratio (Sacid:Amine) |
| --- | --- | --- | --- |
| SAmide-1 | SAcid-6 | TEPA | 1:0.25 |
| SAmide-2 | SAcid-1 | TEPA | 1:0.33 |
| SAmide-3 | SAcid-2 | TEPA | 1:0.33 |
| SAmide-4 | SAcid-2 | TEPA | 1:0.5 |
| SAmide-5 | SAcid-6 | TEPA | 1:0.5 |
| SAmide-6 | SAcid-5 | TEPA | 1:0.5 |
| SAmide-7 | SAcid-2 | AGBC | 1:1 |
| SAmide-8 | SAcid-3 | APDEA | 1:1 |
| SAmide-9 | SAcid-6 | AEEA | 1:1 |
| SAmide-10 | SAcid-6 | DEA | 1:1 |
| SAmide-11 | SAcid-7 | TEPA | 1:0.5 |
| Samide-12 | SAcid-9 | TEPA | 1:0.5 |

Heavy-duty diesel style lubricant formulations containing the succinimide-amide reaction products, described above in Table II, were evaluated in dispersant bench tests, the Spot Dispersancy Test (SDT) and Soot Thickening Test (STT). The impact on viscometrics (Kinematic Viscosity at 100° C. (KV100) and Cold Cranking Simulator (CCS)) of the succinimide-amide reaction products on PCMO style formulations was also evaluated.

Spot Dispersancy Test

The Spot Dispersancy Test affords a measure of an additive's ability to disperse sludge. In the Spot Dispersancy Test, a dispersant candidate is mixed with an amount of Sequence VE sludge oil and is incubated at 300° F. for 16 hours. The resulting mixture (3–10 drops) is dropped onto a standard white blotter paper producing a sludge/oil spot. After 24 hours, the diameter of the sludge and the oil rings are measured. As dispersancy is the ability of an oil to keep sludge in suspension, dispersancy in the Spot Dispersancy Test is reflected by the difference in diameters of the sludge and oil rings. The sludge ring being nearly as wide as the oil ring reflects high dispersancy. Multiplying the quotient of the sludge ring and the oil ring diameters by 100 produces a rating (SDT Rating). A high numerical rating is indicative of good dispersance. Table III depicts the Spot Dispersancy Test performance of several additives of the present invention. All of the dispersants were added to the sludge oil in an amount of 4 wt. %.

TABLE III

Spot Dispersancy Test Results for succinimide-amides

| Sample # | Dispersant | SDT Rating |
| --- | --- | --- |
| 1* | none | 25.6 |
| 2* | Mannich control | 60.4 |
| 3 | SAmide-3 | 74.2 |
| 4 | SAmide-4 | 75.4 |
| 5 | SAmide-7 | 73.5 |
| 6 | SAmide-8 | 75.0 |
| 7 | SAmide-11 | 73.5 |
| 8 | Samide-12 | 71.9 |

The test procedure is described in Example 1 of U.S. Pat. No. 4,908,145. The Mannich control dispersant afforded a SDT rating of 60.4. These commercial Mannich products exhibit excellent dispersancy in gasoline engine test performance (Sequence VE and Sequence IIIE) and excellent diesel engine test performance. A Spot Dispersant Test Rating above 60, therefore, with 4 wt. % added dispersant is indicative of good dispersancy. As indicated in Table III, the additives of this invention would likewise be expected to afford excellent dispersancy.

Viscosity Index Credit

Additives of this invention, a commercially-available Mannich dispersant, and a commercially-available succinimide dispersant were blended into a motor oil formulation containing metal-sulfonates, zinc dithiophosphate wear inhibitors, sulfur containing antioxidants, a pour point depressant, and a viscosity index improver. Additives of the invention and the commercial Mannich dispersant were of nearly equal activities (approximately 40 wt. %), while the commercial succinimide dispersant had a higher activity of 65 wt. %.

Table IV details the viscosity index improving credit advantages exhibited by several dispersants of this invention. For oils formulated as described above, 4.9 wt. % of the Mannich dispersant or the succinimide dispersant required 7.5 wt. % of a commercially-available non-dispersant olefin copolymer viscosity index improver to meet a viscosity target of 10.0 to 10.6 cSt (centistokes). On the other hand, the dispersants additives of the invention required lower amounts (3 to 8 wt. % less) of this same viscosity index improver to meet or exceed the 100° C. viscosity target. The dispersants of the present invention advantageously impart blending versatility by addressing both the low and high temperature 5W-30 specifications.

Soot Thickening Test (STT) Performance

The ability of the dispersants of this invention to disperse soot and soot induced oil thickening was measured in a soot thickening bench test. In this test, the dispersant in a fully formulated 15W-40 lubricant composition is sheared in the presence of carbon black, a soot mimic. The lubricating compositions for the STT contain the test dispersant at 6.5 wt. % on an as is basis, as well as metal-containing sulfonates, zinc dithiophosphate wear inhibitors, sulfur containing antioxidants, a pour point depressant, and a viscosity index improver. The viscosity of the sooted mixture and its fresh oil analog is measured at 100° C. using a capillary viscometer. The percent viscosity increase is calculated by comparing the viscosity of the fresh oil and its counterpart treated with carbon black. Lower percent viscosity increases are indicative of better soot dispersancy.

Table IV also sets forth the kinematic viscosities and the results of the cold cranking simulator (CCS) for various passenger car motor oil (PCMO) lubricating oil formulations. In the examples, 4.9 percent by weight of the dispersants indicated in Table IV were added to identical lubricating oil formulations containing an SAE 5W-30 mineral oil basestock having the same detergent-inhibitor package. A commercially-available non-dispersant olefin copolymer viscosity index improver was added to meet a viscosity target of 10.0 to 10.6 cSt (centistokes). The amount of added viscosity index improver (VII) is set forth in the Table. A reduction in low temperature viscosity, as indicated by the Cold Cranking Simulator test, is indicative of good low temperature properties.

TABLE IV

Evaluation of Succinimide-Amide reaction products

| Run | Succinimide-Amide Reaction Products | Added VII (wt. %) | KV100 | CCS @ −25° C. | STT |
|---|---|---|---|---|---|
| 1 | SAmide-1 | 7.5 | 11.06 | 3370 | 63.0 |
| 2 | SAmide-3 | 6.8 | 10.39 | 3500 | 69.4 |
| 3 | SAmide-4 | 7.1 | 10.57 | 3520 | 61.76 |
| 4 | SAmide-7 | 6.8 | 10.56 | 3410 | N.A. |
| 5 | SAmide-8 | 7.5 | 10.88 | 3340 | N.A. |
| 6 | SAmide-9 | 7.5 | 10.82 | 3350 | N.A. |
| 7 | SAmide-12 | 7.5 | 11.06 | 3370 | 52.3 |
| 8* | PIBSA/ APDEA (1:1) | 7.5 | 10.85 | 3410 | N.A. |
| 9* | Mannich Control | 7.5 | 10.82 | 3620 | N.A. |
| 10* | Succinimide Control | 7.5 | 10.04 | 3460 | N.A. |
| 11* | Mixed dispersant Control[1] | — | N.A. | NA. | 80.2 |

*Comparative Example
[1]STT control utilized a mixture of commercially-available dispersants.

The additives of the present invention impart equivalent or higher 100° C. viscosities to motor oil formulations compared to the two commercial dispersants by virtue of the advantageous higher molecular weight of the additives of this invention. More importantly, the dispersants of this invention impart 100° C. viscosity lift to finished oils with no adverse effects on low temperature viscometrics.

The additives of this invention contribute viscosity index credit to finished oils, reducing the amount of conventional viscosity index improver required to achieve a desired viscosity target. Reducing the amount of viscosity index improver in a motor oil can thus offer both cost and engine cleanliness advantages. Further, the low CCS viscosities obtained in compositions of the present invention allows one to formulate lubricating oil compositions containing less or even no unconventional, i.e., synthetic, oils such as poly-alpha-olefins, and still meet the performance requirements set forth for crankcase lubricating oils. The unexpected ability to formulate lubricating oils according to the present invention using higher amounts of mineral oil, without a decrease in performance, results in more formulation flexibility as well as cost savings.

Examples of Succinimide-Ester Dispersants

The succinimide-ester reaction products set forth in Table V were prepared as follows:

The alkoxylated amine and succinimide-acid compounds, as set forth in Table V, were combined with process oil in a suitable reaction vessel and heated to between 140 and 180° C. under nitrogen. The reaction generally required 4 to 8 hours for formation of the esters products. The molar ratio of succinimide-acid compound to alkoxylated amine used is set forth in the Table.

A representative example of a suitable preparation method for the succinimide-esters is as follows:

Example: Preparation of SEster-1

A 500 mL resin kettle equipped with overhead stirrer, Dean Stark trap and thermometer was charged with 182.7 g of SAcid-3, and 6.3 g of a fully propoxylated triethylene tetraamine (TETA-4PO). The reaction mixture was heated to 160° C. with stirring under a continual nitrogen purge. The reaction temperature was then raised to and held at 180° C. for 3 hours. Residual water was removed in vacuo to afford 182 g of product.

TABLE V

Succinimide-Ester (SEster) Reaction Products

| Sample | Succinimide- Acid | Alkoxylated Amine | Ratio (SAcid: alkoylated amine) |
|---|---|---|---|
| SEster-1 | SAcid-3 | TETA-4PO | 1:0.33 |
| SEster-2 | SAcid-3 | TETA-4PO | 1:0.5 |
| SEster-3 | SAcid-5 | TETA-4PO | 1:0.5 |
| SEster-4 | SAcid-6 | TETA-4PO | 1:0.5 |
| SEster-5 | SAcid-5 | HMDA-4PO | 1:0.5 |
| SEster-6 | SAcid-3 | HMDA-4PO | 1:0.5 |
| SEster-7 | SAcid-6 | HMDA-4PO | 1:0.5 |
| SEster-8 | SAcid-6 | TEA | 1:1 |
| SEster-9 | SAcid-7 | TETA-4PO | 1:0.5 |
| SEster-10 | SAcid-7 | HMDA-4PO | 1:0.5 |
| SEster-11 | SAcid-9 | TETA-4PO | 1:0.5 |

The succinimide-ester reaction products, described above in Table V, were evaluated in dispersant bench tests, the Spot Dispersancy Test (SDT) and Soot Thickening Test (STT). Their impact on viscometrics (Kinematic Viscosity at 100° C. (KV100) and Cold Cranking Simulator (CCS) of PCMO formulations was also evaluated. The results are set forth in Table VI.

TABLE VI

Evaluation of Succinimide-Ester reaction products

| Run | Succinimide-Ester Reaction Products | SDT | KV100 | CCS @ −25° C. | STT |
|---|---|---|---|---|---|
| 1 | SEster-1 | 75.0 | 10.65 | 3400 | 45.1 |
| 2 | SEster-2 | 78.8 | 10.72 | 3250 | 36.15 |
| 3 | SEster-9 | 74.3 | 10.72 | 3410 | 48.21 |
| 4 | SEster-4 | 77.6 | 10.87 | 3240 | 37.75 |
| 5 | SEster-10 | 71.4 | 10.85 | 3470 | N.A. |
| 6 | SEster-6 | 74.3 | 10.76 | 3240 | 75.0 |
| 7 | SEster-7 | 74.3 | 10.78 | 3310 | 59.1 |
| 8 | SEster-8 | 74.2 | 10.70 | 3410 | N.A. |

TABLE VI-continued

Evaluation of Succinimide-Ester reaction products

| Run | Succinimide-Ester Reaction Products | SDT | KV100 | CCS @ −25° C. | STT |
|---|---|---|---|---|---|
| 9 | SEster-11 | 79.5 | 10.87 | 3730 | 21.7 |
| 10* | Mannich Control | 60.4 | 10.82 | 3620 | N.A. |
| 11* | Succinimide Control | N.A. | 10.04 | 3460 | N.A. |
| 12* | Mixed dispersant | N.A. | N.A. | N.A. | 80.2 |

*Comparative Examples
Candidates were tested at a treat rate of 4% in the SDT.
PCMO formulation at 2.009% active dispersant and 7.5% VI improver for KV100 and CCS.

The succinimide-esters of the present invention exhibit superior dispersant properties (i.e., higher SDT results) compared to the Mannich control according to the Spot Dispersancy Test.

The succinimide-ester additives of the present invention impart equivalent or higher 100° C. viscosities to motor oil formulations compared to the two commercial dispersants by virtue of the advantageous higher molecular weight of the additives of this invention. More importantly, the dispersants of this invention impart 100° C. viscosity lift to finished oils with no adverse effects on low temperature viscometrics.

The succinimide-ester additives of this invention contribute viscosity index credit to finished oils, reducing the amount of conventional viscosity index improver required to achieve a desired viscosity target. Reducing the amount of viscosity index improver in a motor oil can thus offer both cost and engine cleanliness advantages. Further, the low CCS viscosities obtained in compositions of the present invention allows one to formulate lubricating oil compositions containing less or even no unconventional, i.e., synthetic, oils such as poly-alpha-olefins, and still meet the performance requirements set forth for crankcase lubricating oils. The unexpected ability to formulate lubricating oils according to the present invention using higher amounts of mineral oil, without a decrease in performance, results in more formulation flexibility as well as cost savings.

Increasing the Molecular Weight of Amine-Based Dispersants

The pendant carboxylic acid moiety of the succinimide-acid compound can undergo reaction with amine containing dispersants to generate higher molecular weight lubricating oil dispersants.

Examples of dispersants that may be modified include any amine dispersants having a reactive (i.e., unhindered primary and/or secondary) amine group. Suitable dispersants include mono- and bis-succinimides, Mannich condensation products, hydrocarbyl amines (such as polybutene amines) and polyether amines. Reaction with the pendant carboxylic acid moiety of the succinimide-acid compound with the amine dispersant will result in an amide bond. This new compound will have a three-dimensional shape and an increased molecular weight.

The reactants are preferably used in amounts so as to provide a ratio of acid groups on the succinimide-acid compound to dispersant in the range of from n:1 to 0.1:1 where n is the number of reactive nitrogen atoms present in the dispersant.
The modified amine dispersants in the following examples were prepared as follows:
The amine dispersant and succinimide-acid compounds, as set forth in Table VII, were combined with process oil in a suitable reaction vessel and heated to between 160 and 180° C. under nitrogen. The reaction generally required 4 to 8 hours for formation of the succinimide-amide products. The molar ratio of succinimide-acid compound to the amine dispersant is set forth in the Table.

A representative example of a suitable method of preparing the modified amine dispersants is as follows.

Example: Preparation of MAD-1

A 500 mL resin kettle equipped with overhead stirrer, Dean Stark trap, and thermometer was charged with 91.4 g of SAcid-3, 77.8 g of a succinimide dispersant (1.8% N) and 44.3 g of process oil. The reaction mixture was heated to 160° C. with stirring under a continual nitrogen purge. The reaction temperature was raised to and held at 180° C. for 3 hours. Residual water was removed in vacuo to afford 208.2 g of product.

TABLE VII

Modified Amine Dispersants (MAD):

| Sample | Succinimide-Acid | Amine Dispersant | Ratio (SAcid:amine dispersant) |
|---|---|---|---|
| MAD-1 | SAcid-3 | Succinimide[1] | 1:1 |
| MAD-2 | SAcid-3 | Succinimide[1] | 1:0.5 |
| MAD-3 | SAcid-3 | Mannich[2] | 1:1 |
| MAD-4 | SAcid-3 | Mannich[2] | 1:0.5 |
| MAD-5 | SAcid-9 | Mannich[2] | 1:0.5 |

[1]A bis-succinimide derived from 1300 molecular weight polybutene-substituted succinic anhydride and tetraethylene pentamine
[2]A Mannich dispersant comprising the Mannich condensation reaction product of a 2100 molecular weight polybutene phenol and tetraethylene pentamine The succinimide-acid modified amine dispersant, described above in Table VII, were evaluated in dispersant bench tests, the Spot Dispersancy Test (SDT) and Soot Thickening Test (STT). The succinimide-acid modified amine dipsersants were also evaluated for their impact on viscometrics (Kinematic Viscosity at 100° C. (KV 100) and Cold Cranking Simulator (CCS)) of PCMO formulations. All of the PCMO formulations contained 7.5 wt. % of a commercially-available non-dispersant olefin copolymer viscosity index improver and approximately 2 wt. % active dispersant. The results of the evaluation are set forth in Table VIII.

TABLE VIII

Evaluation of the Succinimide-acid Modified Amine Dispersants

| Run | Modified Amine Dispersant | KV100 | CCS | SDT | STT |
|---|---|---|---|---|---|
| 1 | MAD-1 | 10.57 | 3220 | 51.5 | 66.3 |
| 2 | MAD-3 | 10.76 | 3350 | 75.8 | 75.3 |
| 3 | MAD-2 | 10.85 | 3280 | N.A. | 53.5 |
| 4 | MAD-4 | 10.67 | 3280 | 68.2 | 81.8 |
| 5 | MAD-5 | 11.41 | 4013 | 75.8 | N.A. |
| 6* | Succinimide | 10.04 | 3460 | N.A. | N.A. |
| 7* | Mannich | 10.45 | 3600 | 66.7 | 80.2[1] |

*Comparative examples
[1]Mixed dispersant control described in footnote 1 of Table IV.

The succinimide-acids of the present invention allow for the preparation of significantly higher molecular weight dispersants (50 to 100% higher) than is available from the conventional approach of preparing bis-succinimide or Mannich dispersants.

The modified amine dispersants of the present invention impart higher 100° C. viscosities to motor oil formulations compared to the two commercial dispersants by virtue of the advantageous higher molecular weight of the additives of this invention. More importantly, the dispersants of this invention impart 100° C. viscosity lift to finished oils with no adverse effects on low temperature viscometrics.

The additives of this invention contribute viscosity index credit to finished oils, reducing the amount of conventional viscosity index improver required to achieve a desired viscosity target. Reducing the amount of viscosity index improver in a motor oil can thus offer both cost and engine cleanliness advantages. Further, the low CCS viscosities obtained in compositions of the present invention allows one to formulate lubricating oil compositions containing less or even no unconventional, i.e., synthetic, oils such as poly-alpha-olefins, and still meet the performance requirements set forth for crankcase lubricating oils. The unexpected ability to formulate lubricating oils according to the present invention using higher amounts of mineral oil, without a decrease in performance, results in more formulation flexibility as well as cost savings.

Preparation of Lubricity Additives

Problems associated with fuel lubricity arose in the mid-1960's when a number of aviation fuel pump failures occurred. After considerable research, it was realized that advances in the refining of aviation turbine fuel had resulted in the almost complete removal of the naturally occurring lubricating components from the fuel. The removal of these natural lubricants resulted in the seizure of fuel pump parts. By the mid-1980's, it seemed likely that a similar problem was imminent in diesel fuel pumps. Fuel injection pump pressures had been steadily increasing while there was also a growing concern to reduce the sulfur content of the diesel fuel. The desire to reduce the sulfur content of the diesel fuel, in an effort to reduce pollution, required the use of more rigorous fuel refining processes. It was determined that as refining processes became more stringent, the naturally occurring oxygen containing compounds and polyaromatics which contribute to diesel fuel's inherent lubricity were eliminated. In response to these developments, a number of effective lubricity additives were developed for diesel fuels. These additives are now widely used to enhance the lubricity of highly refined, low sulfur diesel fuels.

Gasoline fuels are also becoming subject to compositional constraints, including restrictions on sulfur content, in an effort to reduce pollutants. The principle concern is the effect of sulfur on exhaust catalyst life and performance. The lubricity requirements of gasoline are somewhat lower than for diesel fuel since the majority of gasoline fuel injection systems inject fuel upstream of the inlet valves and thus operate at much lower pressures than diesel fuel pumps. However, as automobile manufacturers desire to have electrically powered fuel pumps within the fuel tanks, failure of the pumps can be expensive to repair. These problems are also likely to increase as injection systems become more sophisticated and the gasoline fuels become more highly refined.

Additional pump wear concerns have arisen with the introduction of vehicles having direct injection gasoline engines since the fuel pumps for these vehicles operate at significantly higher pressures than traditional gasoline fuel pumps.

The succinimide-acid compounds of the present invention are useful as lubricity additives for fuel compositions. These compounds can also be used to form reaction products useful as non-acidic lubricity additives for fuels compositions. The pendant carboxylic acid moiety of the succinimide-acid compound can undergo reaction with hydroxyamines or polyols to generate reaction products containing at least one pendant hydroxyl group useful as lubricity additives for liquid fuels. When preparing compounds for use as lubricity additives, it is preferred to use succinimide-acid compounds derived from a low molecular alkyl or alkenyl succinic acylating agents, preferably $C_8$–$C_{100}$ alkenyl succinic anhydrides, more preferably $C_{12}$–$C_{30}$ alkenyl succinic anhydrides and most preferably $C_{16}$–$C_{26}$ alkenyl succinic anhydrides.

Compounds suitable for reaction with the succinimide-acids of the present invention to form non-acidic lubricity additives are hydroxyl-group containing reactants capable of reacting with the succinimide-acid to form a succinimide-ester, a succinimide-amide or mixtures thereof, and which possess at least one pendant hydroxyl group after reaction with the succinimide-acid. The preferred hydroxy-group containing reactants for use in preparing the non-acidic lubricity additives are hydroxyamines; alkoxylated amines; polyols and mixtures thereof. Examples of suitable hydroxyamines include ethanolamine, diethanolamine, triethanolamine, aminoethylethanolamine, aminopropyldiethanolamine, 3-amino-1,2-propanediol, tris(hydroxymethyl)aminomethane, and 2-amino-1,3-propanediol; representative alkoxylated amines include ethoxylated and propoxylated amines and polyamines. An example of these amines includes, for example, 2-(methylamino)ethanol. Suitable polyols include glycerol, sorbitol, pentaerythitol, mannitol and polyalkylene glycols. Most preferred is diethanolamine.

Reaction with the pendant carboxylic acid moiety of the succinimide-acid compound with the hydroxyamines results in esters, amides or mixtures thereof. Reaction with the pendant carboxylic acid moiety of the succinimide-acid compound by the polyols or tertiary amine alkoxides result in an ester bond. The ratio of acid groups on the succinimide-acid compound to hydroxy-group containing reactant ranges from m-1:1 to 1:1, wherein 'm' is the number of hydroxy groups present on the hydroxy-group containing reactant. When 'm' is 1, as in ethanolamine, the ratio of succinimide-acid compound to hydroxy-group containing reactant is preferably 1:1. Regardless of the value of 'm', it is preferred that the molar ratio of succinimide-acid compound to hydroxy-group containing reactant be 1:1. Preferably, when preparing the non-acidic lubricity additives, the molar proportions of the succinimide-acid compound and the hydroxy-group containing reactant are selected such that at least one pendant hydroxyl group remains after reaction.

EXAMPLES

Reaction products set forth in Table IX, suitable for use as lubricity additives, were prepared as follows:

The hydroxyamine and succinimide-acid compounds, set forth in Table IX, were combined with toluene in a suitable reaction vessel and heated at the water/toluene azeotrope reflux temperature, under nitrogen. The reaction generally requires 4 to 8 hours for formation of the reaction products. The molar ratio of succinimide-acid compound to the hydroxyamine is set forth in Table IX.

A representative example of a suitable method of preparing the low molecular weight succinimide-acid derivatives is as follows.

Example: Preparation of LowMW-1

A 1000 mL round bottom flask equipped with overhead stirrer, Dean Stark trap, and thermometer was charged with 96.5 g of SAcid-1, 20.9 g of diethanolamine and 190 g of toluene. The reaction mixture was heated at reflux. After 6 hours 3.2 mL of water was collected. The reaction mixture was concentrated in vacuo to afford 120 g of product.

TABLE IX

Preparation of low molecular weight non-acidic succinimide-acid derivatives (lowMW):

| Sample | Succinimide-Acid | Hydroxyamine | Ratio (SAcid:alkoylated amine) |
|---|---|---|---|
| LowMW-1 | SAcid-1 | DEA | 1:1 |
| LowMW-2 | SAcid-8 | DEA | 1:1 |
| LowMW-3 | SAcid-8 | AEEA | 1:1 |

The efficacy of the reaction products of Table IX as lubricity additives was assessed using the Scuffing Load BOCLE (ball-on-cylinder lubricity evaluator) test (ASTM D 6078–97).

The Scuffing Load BOCLE test allows discrimination and ranking of fuels of differing lubricity. The Scuffing test simulates the severe modes of wear failure encountered in fuel pumps and therefore provides results which are representative of how the fuel would behave in service. The load at which wear failure occurs is referred to as the scuffing load and is a measure of the inherent lubricity of the fuel. The scuffing load is primarily identified by the size and appearance of the wear scar on the ball, which is considerably different in appearance to that found under milder non-scuffing conditions. Fuels giving a high scuffing load on failure have better lubricating properties than fuels giving a low scuffing load on failure. All tests were conducted in a Jet A fuel containing 100 ppm w/w of the reaction products as set forth in the following Table.

Table X demonstrates the effectiveness of the additives of the present invention as lubricity additives. Higher Scuffing Load BOCLE values are indicative of improved lubricity.

TABLE X

Evaluation of lubricity properties for low molecular weight succinimide-acid and derivatives thereof

| Run | Sample | BOCLE |
|---|---|---|
| 1 | LowMW-1 | 2200 |
| 2 | LowMW-2 | 2400 |
| 3 | LowMW-3 | 2800 |
| 4 | SAcid-1 | 2800 |
| 5 | SAcid-8 | 1800 |
| 6 | SAcid-4 | 2200 |
| 7* | Clear fuel-no additive | 1200 |

*Comparative Examples

It is clear, upon examination of the data in Table X, that the fuel composition containing the additives of the present invention exhibit improved lubricity as compared to base fuel alone. The succinimide-acid deriviatives (set forth in Runs 1–3, in addition to their lubricity benefits, have the added advantage of being non-acidic.

Preparation of Friction Modifiers

The pendant carboxylic acid moiety of the succinimide-acid compound can undergo reaction with polyamines, hydroxyamines and polyhydroxyl containing compounds (polyols) to prepare compounds useful as friction modifiers. These additives can be useful in numerous formulations where friction modifiers are required including automatic transmission fluids, continuously variable transmission fluids, passenger car motor oils, heavy duty diesel engine oils, gear oils and medium speed diesel engine oils. When preparing compounds for use as friction modifiers in lubricating oil compositions, it is preferred to use succinimide-acid compounds derived from a low molecular alkyl or alkenyl succinic acylating agents, preferably $C_8$–$C_{100}$ alkenyl succinic anhydrides, more preferably $C_{12}$–$C_{30}$ alkenyl succinic anhydrides and most preferably $C_{16}$–$C_{26}$ alkenyl succinic anhydrides.

An example of a polyamine utilized in this disclosure for the preparation of friction modifiers is aminoguanidine. Reaction of the pendant carboxylic acid moiety of the succinimide-acid compound and aminoguanidine results in an amide bond. Preferably, the molar ratio of aminoguanidine to succinimide-acid is approximately 1:1.

Examples of hydroxyamines that may be used include ethanolamine, diethanolamine, aminoethylethanolamine, aminopropyldiethanolamine, 3-amino-1,2-propanediol tris (hydroxymethyl)aminomethane, and 2-amino-1,3-propanediol.

Reaction with the pendant carboxylic acid moiety of the succinimide-acid compound by the amine moiety of the hydroxyamine results in amides, esters or mixtures thereof.

Examples of polyhydroxyl containing compounds (polyols) include glycerol, sorbitol, pentaerythritol, triethanolamine and mannitol.

Reaction with the pendant carboxylic acid moiety of the succinimide-acid compound by the hydroxyl moiety of the polyol results in an ester bond. The ratio of acid groups on the succinimide-acid compound to hydroxyl-group containing reactant (i.e. hydroxyamine or polyol) ranges from m-1:1 to 1:1, wherein 'm' is the number of hydroxy groups present on the hydroxy-group containing reactant. When 'm' is 1, as in ethanolamine, the ratio of succinimide-acid compound to hydroxy-group containing reactant is preferably 1:1. Regardless of the value of 'm', it is preferred that the molar ratio of succinimide-acid compound to hydroxy-group containing reactant be 1:1. It is desirable to select the molar proportions of the succinimide-acid compound and the hydroxy-group containing reactant are selected such that at least one pendant hydroxyl group remains after reaction.

Reaction products suitable as friction modifiers were prepared as follows:

The polyamine, succinimide-acid compound and process oil were combined and heated to 180° C. under nitrogen. The reaction generally required 4 to 8 hours for formation of the succinimide-amide product or succinimide-ester product.

A representative example of a suitable method of preparing the succinimide-amide friction modifiers is as follows.

Example: Preparation of FM-1

A 1000 mL resin kettle equipped with overhead stirrer, dean stark trap, and thermometer was charged with 88 g of SAcid-1, 27.2 g of aminoguanidine bicarbonate and 99.2 g of process oil. The mixture was heated to 70° C. for 30 minutes. The reaction temperature was raised to 120° C. for 30 minutes and then raised to and held at 160° C. for 2 hours. Residual water was removed in vacuo to afford 188 g of product.

TABLE XI

Synthesized Succinimide-amide Friction Modifiers (FM):

| Sample | Succinimide-acid | Polyamine | Ratio (succinimide-acid:polyamine) |
|---|---|---|---|
| FM-1 | SAcid-1 | AGBC | 1:1 |
| FM-2 | SAcid-1 | DEA | 1:1 |
| FM-3 | SAcid-8 | DEA | 1:1 |
| FM-4 | SAcid-8 | AEEA | 1:1 |
| FM-5 | SAcid2 | AGBC | 1:1 |

Aminoguanidine amides have been shown to be excellent silver lubricity additives in Medium Speed Diesel formulations (see, for example, U.S. Pat. No. 4,948,523). Current commercially available aminoguanidine amide is a biphasic oil/paste. The aminoguanidine amides prepared as described above are clear homogenous oils.

Preparation of Detergent Additives for Liquid Fuels

The pendant carboxylic acid moiety of the succinimide-acid compound can undergo reaction with polyamines to generate useful gasoline detergent additives including intake valve deposit control additives for spark-ignition internal combustion engines including direct injection gasoline engines as well as detergent additives for fuels, such as diesel fuel, for use in compression-ignition engines. When preparing compounds for use as fuel detergents, it is preferred to use succinimide-acid compounds derived from an polyalkyl or polyalkenyl succinic acylating agent having a number average molecular weight of from 500 to 3000, preferably 800 to 2100. Preferred polyalkyl and polyalkenyl groups include polypropylene and polyisobutylene.

Examples of polyamines suitable for use in preparing succinimide-amides for use as fuel detergents include those polyamines known in the art for use in preparing fuel detergents as taught, for example, in U.S. Pat. Nos. 3,948, 619; 5,634,951 and 5,725,612. Preferred amines include 3-dimethylaminopropylamine, aminoethylethanolamine, aminopropyl diethanolamine, diethylene triamine, triethylene tetramine, and tetraethylene pentamine. Reaction with the pendant carboxylic acid moiety of the succinimide-acid compound by the amine results in an amide bond. The ratio of succinimide-acid compound to polyamine ranges from n:1 to 1:1 where n is the number of reactive nitrogen atoms (i.e., unhindered primary and secondary amines capable of reacting with the succinimide-acid) within the polyamine. It is preferred that the molar ratio of succinimide-acid compound to polyamine be 1:1.

A typical method for preparing compounds suitable for use as fuel detergents from the succinimide-acids of the present invention is as follows:

The polyamine, succinimide-acid compound and toluene are combined and heated at the water/toluene azeotrope reflux, under nitrogen. The reaction generally requires 2 to 10 hours for formation of the succinimide-amide product. Aromatic 150 can be utilized instead of toluene in this reaction.

A representative example of a suitable method of preparing the succinimide-amides suitable for use as fuel detergents is as follows.

Example: Preparation of FuelDet-1

A 2 L round bottom flask equipped with overhead stirrer, Dean Stark trap, was charged with 278.4 g of SAcid-4 and 20.4 g of dimethylaminopropylamine and 300 g of toluene. The mixture was stirred and heated at reflux. After 6 hours 3.2 mL of water was collected. The reaction mixture was concentrated in vacuo to afford 261 g of product.

TABLE XII

Synthesized Fuel Detergents (FuelDet)

| Sample | Succinimide-acid | Polyamine | Ratio (succinimide-acid:polyamine) |
|---|---|---|---|
| FuelDet-1 | SAcid-4 | DMAPA | 1:1 |
| FuelDet-2 | SAcid-4 | TETA | 1:0.5 |

The products of Table XII are expected to be effective detergent additives for use in fuels for spark-ignition engines, including direct injection gasoline engines, and compression-ignition engines.

Preparation of Antioxidants

The pendant carboxylic acid moiety of the succinimide-acid compound can undergo reaction with polyamines to prepare compounds useful as antioxidants. These additives can be useful in numerous formulations where antioxidants are required including spark-ignition fuels, compression-ignition fuels, automatic transmission fluids, continuously variable transmission fluids, passenger car motor oils, heavy duty diesel engine oils, gear oils and medium speed diesel engine oils. When preparing compounds for use as antioxidants in lubricating oil and fuel compositions, it is preferred to use succinimide-acid compounds derived from a low molecular alkyl or alkenyl succinic acylating agents, preferably $C_8$–$C_{100}$ alkenyl succinic anhydrides, more preferably $C_{12}$–$C_{30}$ alkenyl succinic anhydrides and most preferably $C_{16}$–$C_{26}$ alkenyl succinic anhydrides.

Polyamines particularly suitable for the preparation of antioxidants include N-arylphenylenediamines, such as N-phenylphenylenediamines, for example, N-phenyl-1,4-phenylenediamine, N-phenyl-1,3-phenylendiamine, and N-phenyl-1,2-phenylenediamine; aminothiazoles such as aminothiazole, aminobenzothiazole, aminobenzothiadiazole and aminoalkylthiazole; aminocarbazoles; aminoindoles; aminopyrroles; amino-indazolinones; aminomercaptotriazoles; aminoperimidines; aminoalkyl imidazoles, such as 1-(2-aminoethyl) imidazole, 1-(3-aminopropyl) imidazole; and aminoalkyl morpholines, such as 4-(3-aminopropyl) morpholine.

In a preferred embodiment, the compounds suitable for use as antioxidants are prepared from succinimide-acids obtained by reacting a low molecular alkyl or alkenyl succinic acylating agents, preferably $C_8$–$C_{70}$ alkenyl succinic anhydrides, with an aromatic amino acid.

Preparation of Metal Detergent Additives

The pendant carboxylic acid moiety of the succinimide-acid compound can undergo neutralization reaction with an alkali or alkaline-earth metal oxide or hydroxide to result in a simple metal salt. This neutralization reaction or the pendant carboxylic acid moiety can also be performed in the presence of carbon dioxide resulting in an overbased metal salt. When preparing compounds for use as metal-containing detergents, it is preferred to use succinimide-acid compounds derived from a low molecular alkyl or alkenyl succinic acylating agents, preferably $C_8$–$C_{100}$ alkenyl succinic anhydrides, more preferably $C_{12}$–$C_{30}$ alkenyl succinic anhydrides and most preferably $C_{16}$–$C_{26}$ alkenyl succinic anhydrides.

These sulfur-free additives are expected to be effective detergents useful for lubricant formulations including crankcase, gear, CVT and ATF applications.

Detergents in the lubricating oils suspend thermal decomposition and oxidation products and reduce or retard the formation of varnish and lacquer deposits.

The base fuels used in formulating the fuel compositions of the present invention include any base fuels suitable for use in the operation of spark-ignition or compression-ignition internal combustion engines such as diesel fuel, jet fuel, kerosene, leaded or unleaded motor and aviation gasolines, and so-called reformulated gasolines which typically contain both hydrocarbons of the gasoline boiling range and fuel-soluble oxygenated blending agents, such as alcohols, ethers and other suitable oxygen-containing organic compounds. Oxygenates suitable for use in the present invention include methanol, ethanol, isopropanol, t-butanol, mixed C1 to C5 alcohols, methyl tertiary butyl ether, tertiary amyl methyl ether, ethyl tertiary butyl ether and mixed ethers. Oxygenates, when used, will normally be present in the base fuel in an amount below about 25% by volume, and preferably in an amount that provides an oxygen content in the overall fuel in the range of about 0.5 to about 5 percent by volume.

The base fuels used in formulating the fuel compositions of the present invention include compression ignition fuels having a sulfur content of up to about 0.2% by weight, more preferably up to about 0.05% by weight, as determined by the test method specified in ASTM D 2622-98. The preferred compression-ignition fuels for use in the present invention are low sulfur content diesel fuels.

The base oils suitable for use in formulating lubricating oil compositions to the present invention may be selected from any of the synthetic or natural oils or mixtures thereof. The synthetic base oils include alkyl esters of dicarboxylic acids, polyglycols and alcohols, poly-alpha-olefins, including polybutenes, alkyl benzenes, organic esters of phosphoric acids, and polysilicone oils. Natural base oils include mineral lubrication oils which may vary widely as to their crude source, e.g., as to whether they are paraffinic, naphthenic, or mixed paraffinic-naphthenic. The base oil typically has a viscosity of about 2.5 to about 15 cSt and preferably about 2.5 to about 11 cSt at 100° C.

The additives used in formulating the compositions of the present invention can be blended into the base oil or fuel individually or in various sub-combinations. However, it is preferable to blend all of the components concurrently using an additive concentrate (i.e., additives plus a diluent, such as a hydrocarbon solvent). The use of an additive concentrate takes advantage of the mutual compatibility afforded by the combination of ingredients when in the form of an additive concentrate. Also, the use of a concentrate reduces blending time and lessens the possibility of blending errors.

In one embodiment, the present invention is directed to a method of improving the oxidation stability and retarding the rate of viscosity increase, of a lubricating oil, wherein said method comprises adding to a lubricating oil an oxidation stability improving amount of the succinimide-acid derivatives of the present invention, wherein said oxidation stability improving amount of said succinimide-acid derivative is effective to improve the oxidative stability of the lubricating oil, as compared to the same lubricating oil except that it is devoid of said succinimide-acid derivative. For improving the oxidation stability of the oil, the succinimide-acid derivative is typically present in the lubricating oil in an amount of from 0.1 to 3 weight percent based on the total weight of the oil. Improvements in the oxidation stability of a lubricating oil are evident by a reduction in the rate of oil thickening of an oil containing the additives of the present invention as well as a reduction in the amount of insoluble deposit forming materials in the oil compared to a similar oil except that it is devoid of said additive.

In one embodiment, the present invention is directed to a method of improving the fuel economy of an internal combustion engine, wherein said method comprises using as the crankcase lubricating oil for said internal combustion engine a lubricating oil containing the succinimide-acid derivative of the present invention, wherein said succinimide-acid derivative is present in an amount sufficient to improve the fuel economy of the internal combustion engine using said crankcase lubricating oil, as compared to said engine operated in the same manner and using the same crankcase lubricating oil except that the oil is devoid of said succinimide-acid derivative. For improving fuel economy, the succinimide-acid derivative is typically present in the lubricating oil in an amount of from 0.1 to 3 weight percent based on the total weight of the oil.

In one embodiment, the present invention is directed to a method of reducing deposits on a lubricated surface, wherein said method comprises using as the lubricating oil for said surface a lubricating oil containing the succinimide-acid derivative of the present invention, wherein said succinimide-acid derivative is present in an amount sufficient to reduce the amount of deposits on said surface, as compared to the amount of deposits on said surface subjected to the same operating conditions and using the same lubricating oil except that the oil is devoid of said succinimide-acid derivative. For reducing deposits, the succinimide-acid derivative is typically present in the lubricating oil in an amount of from 0.1 to 10 weight percent based on the total weight of the oil. Representative of the deposits that may be reduced using the compositions of the present invention include piston deposits, ring land deposits, crown land deposits and top land deposits.

In one embodiment, the present invention is directed to a method of reducing wear in an internal combustion engine, wherein said method comprises using as the crankcase lubricating oil for said internal combustion engine a lubricating oil containing the succinimide-acid derivative of the present invention, wherein said succinimide-acid derivative is present in an amount sufficient to reduce the wear in an internal combustion engine operated using said crankcase lubricating oil, as compared to the wear in said engine operated in the same manner and using the same crankcase lubricating oil except that the oil is devoid of said succinimide-acid derivative. For reducing wear, the succinimide-acid derivative is typically present in the lubricating oil in an amount of from 0.1 to 3 weight percent based on the total weight of the oil. Representative of the types of wear that may be reduced using the compositions of the present invention include cam wear and lifter wear.

At numerous places throughout this specification, reference has been made to a number of U.S. Patents and published foreign patent applications. All such cited documents are expressly incorporated in full into this disclosure as if fully set forth herein.

This invention is susceptible to considerable variation in its practice. Accordingly, this invention is not limited to the specific exemplifications set forth hereinabove. Rather, this invention is within the spirit and scope of the appended claims, including the equivalents thereof available as a matter of law.

The patentee does not intend to dedicate any disclosed embodiments to the public, and to the extent any disclosed modifications or alterations may not literally fall within the scope of the claims, they are considered to be part of the invention under the doctrine of equivalents.

I claim:

1. A succinimide-acid derivative prepared by reacting a succinimide-acid compound comprising the reaction product of a hydrocarbyl-substituted succinic acylating agent and an amino acid represented by the formula:

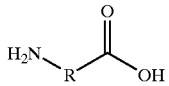

wherein R is an alkyl group, having from 1 to 12 carbon atoms or an aryl group and a compound comprising at least one primary or secondary amine capable of reacting with said succinimide-acid.

2. The succinimide-acid derivative of claim 1, wherein the hydrocarbyl-substituted acylating agent is an alkenyl succinic anhydride comprising from 8 to 100 carbon atoms in the alkenyl group.

3. The succinimide-acid derivative of claim 1, wherein the hydrocarbyl-substituted succinic acylating agent comprises a polyolefin-substituted succinic acylating agent.

4. The succinimide-acid derivative prepared of claim 1, wherein the hydrocarbyl-substituted succinic acylating agent comprises an olefin copolymer grafted with maleic anhydride.

5. The succinimide-acid derivative of claim 1, wherein the amine comprises at least one member selected from the group consisting of polyamines and hydroxy amines.

6. The succinimide-acid derivative of claim 5 wherein the amine comprises a polyethylene polyamine selected from the group consisting of diethylene triamine, triethylene tetramine, tetraethylene pentamine, pentaethylene hexamine, heavy polyamines and mixtures thereof.

7. The succinimide-acid derivative of claim 5 wherein the amine comprises at least one hydroxyamine selected from the group consisting of aminoethylethanolamine, aminopropyl diethanolamine, 3-amino-1,2-propanediol, tris(hydroxymethyl)aminomethane, 2-amino-1,3-propanediol, ethanolamine, diethanolamine and partially propoxylated hexamethylene diamine.

8. The succinimide-acid derivative of claim 5 wherein the amine comprises at least one member selected from the group consisting of N-arylphenylenediamines, aminothiazoles, aminocarbazoles, aminoindoles, aminopyrroles, amino-indazolinones, aminomercaptotriazoles, aminoperimidines, aminoalkyl imidazoles and aminoalkyl morpholines.

9. The succinimide-acid derivative of claim 5 wherein the amine comprises aminoguanidine.

10. The succinimide-acid derivative of claim 5 wherein the amine comprises a polyamine having at least one primary or secondary amino group and at least one tertiary amino group in the molecule.

11. The succinimide-acid derivative of claim 10 wherein the amine comprises at least one member selected from the group consisting of N,N,N",N"-tetraalkyldialkylenetriamines, N,N,N',N"-tetraalkyltrialkylenetetramines, N,N,N',N",N'"-pentaalkyltrialkylenetetramines, and tris(dialkylaminoalkyl)aminoalkylmethanes, wherein the alkyl groups are the same or different and contain no more than about 12 carbon atoms each.

12. The succinimide-acid derivative of claim 10 wherein the amine comprises at least one member selected from the group consisting of dimethylaminopropylamine and N-methyl piperazine.

13. The succinimide-acid derivative of claim 1 wherein the amine comprises an amine dispersant.

14. The succinimide-acid derivative of claim 13 wherein the amine dispersant comprises at least one member selected from the group consisting of mono-succinimides, bis-succinimides, Mannich condensation products, hydrocarbyl amines and polyether amines.

15. A lubricant composition comprising an oil of lubricating viscosity and from about 0.1 to 10 wt. %, based on the total weight of the lubricant composition, of the succinimide-acid derivative of claim 2 with at least one member selected from the group consisting of polyhydroxy compounds, compounds comprising at least one primary or secondary amine capable of reacting with said succinimide-acid, and mixtures thereof.

16. A lubricant composition comprising an oil of lubricating viscosity and from about 0.1 to 10 wt. %, based on the total weight of the lubricant composition, of the succinimide-acid derivative of claim 3 with at least one member selected from the group consisting of polyhydroxy compounds, compounds comprising at least one primary or secondary amine capable of reacting with said succinimide-acid, and mixtures thereof.

17. A lubricant composition comprising an oil of lubricating viscosity and from about 0.1 to 10 wt. %, based on the total weight of the lubricant composition, of the succinimide-acid derivative of claim 4 with at least one member selected from the group consisting of polyhydroxy compounds, compounds comprising at least one primary or secondary amine capable of reacting with said succinimide-acid, and mixtures thereof.

18. A fuel composition comprising a hydrocarbonaceous fuel and from about 0.1 to 10 wt. %, based on the total weight of the fuel composition, of the succinimide-acid derivative of claim 2 with at least one member selected from the group consisting of polyhydroxy compounds, compounds comprising at least one primary or secondary amine capable of reacting with said succinimide-acid, and mixtures thereof.

19. A fuel composition comprising a hydrocarbonaceous fuel and from about 0.1 to 10 wt. %, based on the total weight of the fuel composition, of the succinimide-acid derivative of claim 3 with at least one member selected from the group consisting of polyhydroxy compounds, compounds comprising at least one primary or secondary amine capable of reacting with said succinimide-acid, and mixtures thereof.

20. A fuel composition comprising a hydrocarbonaceous fuel and from about 0.1 to 10 wt. %, based on the total weight of the fuel composition, of the succinimide-acid derivative of claim 4 with at least one member selected from the group consisting of polyhydroxy compounds, compounds comprising at least one primary or secondary amine capable of reacting with said succinimide-acid, and mixtures thereof.

21. A method of improving the fuel economy of an internal combustion engine, said method comprising using as the crankcase lubricating oil for said internal combustion engine lubricant composition of claim 15, wherein said succinimide-acid derivative is present in the lubricant composition in an amount sufficient to improve the fuel economy of the internal combustion engine using said crankcase lubricating oil, as compared to said engine operated in the same manner and using the same crankcase lubricating oil except that the oil is devoid of said succinimide-acid derivative.

22. The method of claim 21 wherein the hydrocarbyl-substituted acylating agent is an alkenyl succinic anhydride comprising from 12 to 30 carbon atoms in the alkenyl group.

23. The method of claim 21 wherein the succinimide-acid derivative is prepared by reacting a succinimide-acid compound and an amine compound comprising at least one primary or secondary amine capable of reacting with said succinimide-acid.

24. The method of claim 23 wherein said amine comprises at least one hydroxy amine selected from the group consisting of aminoethylethanolamine, aminopropyl diethanolamine, 3-amino-1,2-propanediol, tris(hydroxymethyl)aminomethane, 2-amino-1,3-propanediol, ethanolamine, diethanolamine and partially propoxylated hexamethylene diamine.

25. The method of claim 23 wherein said amine comprises aminoguanidine.

26. The method of claim 21 wherein the succinimide-acid derivative is prepared by reacting a succinimide-acid compound and a polyhydroxy compound.

27. The method of claim 26 wherein said polyhydroxy compound comprises at least one fully-alkoxylated amine selected from the group consisting of propoxylated hexamethylene diamine, propoxylated triethylene tetramine, tetrakis(2-hydroxypropyl)ethylenediamine and triethanolamine.

28. The method of claim 26 wherein said polyhydroxy compound comprises at least one polyol selected from the group consisting of glycerol, sorbitol, pentaerythritol, mannitol and polyalkylene glycols.

29. The method of claim 21 wherein said succinimide-acid derivative is present in the crankcase lubricating oil in an amount of from 0.1 to 3 weight percent based on the total weight of the crankcase lubricating oil.

30. A method of improving the fuel economy of a vehicle, said method comprising using as a lubricant composition for said vehicle the lubricant composition of claim 15, wherein said succinimide-acid derivative is present in the lubricant composition in an amount sufficient to improve the fuel economy of the vehicle using said lubricating oil composition, as compared to said vehicle operated in the same manner and using the same lubricant composition except that the composition is devoid of said succinimide-acid derivative.

31. The method of claim 30 wherein the hydrocarbyl-substituted acylating agent is an alkenyl succinic anhydride comprising from 12 to 30 carbon atoms in the alkenyl group.

32. The method of claim 30 wherein the succinimide-acid derivative is prepared by reacting a succinimide-acid compound and an amine compound comprising at least one primary or secondary amine capable of reacting with said succinimide-acid.

33. The method of claim 32 wherein said amine comprises at least one hydroxy amine selected from the group consisting of aminoethylethanolamine, aminopropyl diethanolamine, 3-amino-1,2-propanediol, tris(hydroxymethyl)aminomethane, 2-amino-1,3-propanediol, ethanolamine, diethanolamine and partially propoxylated hexamethylene diamine.

34. The method of claim 32 wherein said amine comprises aminoguanidine.

35. The method of claim 30 wherein the succinimide-acid derivative is prepared by reacting a succinimide-acid compound and a polyhydroxy compound.

36. The method of claim 35 wherein said polyhydroxy compound comprises at least one fully-alkoxylated amine selected from the group consisting of propoxylated hexamethylene diamine, propoxylated triethylene tetramine, tetrakis(2-hydroxypropyl)ethylenediamine and triethanolamine.

37. The method of claim 35 wherein said polyhydroxy compound comprises at least one polyol selected from the group consisting of glycerol, sorbitol, pentaerythritol, mannitol and polyalkylene glycols.

38. The method of claim 30 wherein said lubricant composition is a crankcase oil present in the crankcase of said vehicle.

39. The method of claim 30 wherein said lubricant composition is a lubricant composition present in the automotive drivetrain of said vehicle.

40. The method of claim 30 wherein said succinimide-acid derivative is present in the lubricant composition in an amount of from 0.1 to 3 weight percent based on the total weight of the lubricant composition.

41. A method of reducing wear in an internal combustion engine comprising using as the crankcase lubricating oil for said internal combustion engine the lubricant composition of claim 15, wherein said succinimide-acid derivative is present in an amount sufficient to reduce the wear in an internal combustion engine operated using said crankcase lubricating oil, as compared to the wear in said engine operated in the same manner and using the same crankcase lubricating oil except that the oil is devoid of said succinimide-acid derivative.

42. A method of improving the oxidation stability of a lubricating oil composition, said method comprising adding to an oil of lubricating viscosity an oxidation stability improving amount of the succinimide-acid derivative of claim 2, wherein said amount of said succinimide-acid derivative is effective to improve the oxidative stability of the lubricating oil composition, as compared to the same lubricating oil composition except that it is devoid of said succinimide-acid derivative.

43. The method of claim 42 wherein the hydrocarbyl-substituted acylating agent is an alkenyl succinic anhydride comprising from 12 to 30 carbon atoms in the alkenyl group.

44. The method of claim 42 wherein the amine comprises at least one member selected from the group consisting of N-arylphenylenediamines, aminothiazoles, aminocarbazoles, aminoindoles, aminopyrroles, aminoindazolinones, aminomercaptotriazoles, aminoperimidines, aminoalkyl imidazoles and aminoalkyl morpholines.

45. The method of claim 42 wherein the amino-acid comprises at least one aromatic amino acid.

46. The method of claim 42 wherein said succinimide-acid derivative is present in the lubricating oil composition in an amount of from 0.1 to 3 weight percent based on the total weight of the lubricating oil composition.

47. A method of reducing wear in the fuel system of an internal combustion engine comprising using as the fuel for use in said internal combustion engine the fuel composition of claim 18, wherein said succinimide-acid derivative is present in the fuel in an amount sufficient to reduce the wear of the fuel system, as compared to the wear in said fuel system operated in the same manner and using the same fuel except that said fuel is devoid of said succinimide-acid derivative.

48. The method of claim 47 wherein the hydrocarbyl-substituted acylating agent is an alkenyl succinic anhydride comprising from 12 to 30 carbon atoms in the alkenyl group.

49. The method of claim 47 wherein said derivative is prepared by reacting the succinimide-acid with at least one amine and wherein said amine comprises at least one hydroxy amine selected from the group consisting of aminoethylethanolamine, aminopropyl diethanolamine, 3-amino-1,2-propanediol, tris(hydroxymethyl)aminomethane, 2-amino-1,3-propanediol, ethanolamine, diethanolamine and partially propoxylated hexamethylene diamine.

50. The method of claim 47 wherein said derivative is prepared by reacting the succinimide-acid with at least one polyhydroxy compound and wherein said polyhydroxy compound comprises at least one polyol selected from the group consisting of glycerol, sorbitol, pentaerythritol, mannitol and polyalkylene glycols.

51. A lubricant composition comprising an oil of lubricating viscosity and from about 0.1 to 10 wt. %, based on the total weight of the lubricant composition, of a succinimide-acid derivative, wherein said derivative is prepared by reacting a succinimide-acid comprising the reaction product of a hydrocarbyl-substituted succinic acylating agent and an amino acid represented by the formula:

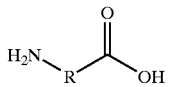

wherein R is an alkyl group, having from 1 to 12 carbon atoms or an aryl group with at least one member selected from the group consisting of polyhydroxy compounds, compounds comprising at least one primary or secondary amine capable of reacting with said succinimide-acid, and mixtures thereof.

52. A method of reducing deposits on a lubricated surface, said method comprising lubricating said surface with the lubricant composition of claim 51, wherein said succinimide-acid derivative is present in an amount sufficient to reduce the amount of deposits on said lubricated surface, as compared to the amount of deposits on said surface subjected to the same operating conditions and lubricated with the same lubricant composition except that the composition is devoid of said succinimide-acid derivative.

53. The method of claim 52 wherein the hydrocarbyl-substituted succinic acylating agent comprises a polyolefin-substituted succinic acylating agent.

54. The method of claim 52 wherein the polyolefin-substituted succinic acylating agent has a number average molecular weight of from 500 to 7000.

55. The method of claim 54 wherein the polyolefin-substituted succinic acylating agent has a number average molecular weight of from 800 to 3000.

56. The method of claim 53 wherein the polyolefin-substituted succinic acylating agent comprises a polyisobutenyl-substituted succinic anhydride.

57. The method of claim 52 wherein the hydrocarbyl-substituted succinic acylating agent comprises an olefin copolymer grafted with maleic anhydride.

58. The method of claim 57 wherein the olefin copolymer has a number average molecular weight of from 1000 to 20,000.

59. The method of claim 52 wherein the succinimide-acid derivative is prepared by reacting a succinimide-acid compound and a compound comprising at least one primary or secondary amine capable of reacting with said succinimide-acid.

60. The method of claim 59 wherein the amine comprises a polyethylene polyamine selected from the group consisting of diethylene triamine, triethylene tetramine, tetraethylene pentamine, pentaethylene hexamine, heavy polyamines and mixtures thereof.

61. The method of claim 59 wherein the amine comprises at least one hydroxyamine selected from the group consisting of aminoethylethanolamine, aminopropyl diethanolamine, 3-amino-1,2-propanediol, tris(hydroxymethyl)aminomethane, 2-amino-1,3-propanediol, ethanolamine, diethanolamine and partially propoxylated hexamethylene diamine.

62. The method of claim 59 wherein the amine comprises at least one member selected from the group consisting of N-arylphenylenediamines, aminothiazoles, aminocarbazoles, aminoindoles, aminopyrroles, aminoindazolinones, aminomercaptotriazoles, aminoperimidines, aminoalkyl imidazoles and aminoalkyl morpholines.

63. The method of claim 59 wherein the amine comprises aminoguanidine.

64. The method of claim 59 wherein the amine comprises an amine dispersant.

65. The method of claim 52 wherein the succinimide-acid derivative is prepared by reacting a succinimide-acid compound and a polyhydroxy compound.

66. The method of claim 65 wherein the polyhydroxy compound comprises a fully-alkoxylated amine.

67. The method of claim 66 wherein the alkoxylated amine comprises at least one member selected from the group consisting of propoxylated hexamethylene diamine, propoxylated triethylene tetramine, tetrakis(2-hydroxypropyl)ethylenediamine and triethanolamine.

68. The method of claim 65 wherein the polyhydroxy compound comprises a polyol.

69. The method of claim 68 wherein the polyol comprises at least one member selected from the group consisting of glycerol, sorbitol, pentaerythritol, mannitol and polyalkylene glycols.

70. The method of claim 52 wherein said lubricated surface is in an internal combustion engine.

71. The method of claim 52 wherein said lubricated surface is in an automotive drivetrain.

72. The method of claim 52 wherein said lubricated surface is an automatic transmission friction plate.

73. A fuel composition comprising a hydrocarbonaceous fuel and from about 0.1 to 10 wt. %, based on the total weight of the fuel composition, of a succinimide-acid derivative, wherein said derivative is prepared by reacting a succinimide-acid comprising the reaction product of a hydrocarbyl-substituted succinic acylating agent and an amino acid represented by the formula:

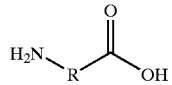

wherein R is an alkyl group, having from 1 to 12 carbon atoms or an aryl group with at least one member selected from the group consisting of polyhydroxy compounds, compounds comprising at least one primary or secondary amine capable of reacting with said succinimide-acid, and mixtures thereof.

74. A method of reducing deposits in the fuel system of an internal combustion engine, said method comprising using as the fuel for said internal combustion engine the fuel composition of claim 53 wherein said succinimide-acid derivative is present in the fuel in an amount sufficient to reduce the deposits in the fuel system, as compared to the amount of deposits in said fuel system operated in the same manner and using the same fuel composition except that said fuel composition is devoid of said succinimide-acid derivative.

75. The method of claim 74 wherein the hydrocarbyl-substituted succinic acylating agent comprises a polyolefin-substituted succinic acylating agent.

76. The method of claim 75 wherein the polyolefin-substituted succinic acylating agent has a number average molecular weight of from 500 to 3000.

77. The method of claim 76 wherein the polyolefin-substituted succinic acylating agent has a number average molecular weight of from 800 to 2100.

78. The method of claim 75 wherein the polyolefin-substituted succinic acylating agent comprises at least one member selected from the group consisting of polyisobutenyl-substituted succinic anhydride and polypropenyl-substituted succinic anhydride.

79. The method of claim 74 wherein the amine comprises a polyamine having at least one primary or secondary amino group and at least one tertiary amino group in the molecule.

80. The method of claim 79 wherein the amine comprises at least one member selected from the group consisting of N,N,N",N"-tetraalkyldialkylenetriamines, N,N,N',N"-tetraalkyltrialkylenetetramines, N,N,N',N",N'"-pentaalkyltrialkylenetetramines, and tris(dialkylaminoalkyl)aminoalkylmethanes, wherein the alkyl groups arc the same or different and contain no more than about 12 carbon atoms each.

81. The method of claim 80 wherein the amine comprises at least one member selected from the group consisting of dimethylaminopropylamine and N-methyl piperazine.

82. The method of claim 74 wherein the amine comprises a polyethylene polyamine selected from the group consisting of diethylene triamine, triethylene tetramine, tetraethylene pentamine, pentaethylene hexamine, heavy polyamines and mixtures thereof.

* * * * *